United States Patent [19]

Gallay et al.

[11] 3,934,017
[45] Jan. 20, 1976

[54] ANTHELMINTIC COMPOSITION AND METHOD UTILIZING ISOTHIOCYANOBENZAZOLES ACTIVE INGREDIENTS

[75] Inventors: Jean-Jacques Gallay, Magden; René Bosshard, Birsfelden; Paul Brenneisen, Basel, all of Switzerland

[73] Assignee: Ciba-Geigy Corporation, Ardsley, N.Y.

[22] Filed: Sept. 3, 1974

[21] Appl. No.: 502,480

Related U.S. Application Data

[62] Division of Ser. No. 311,987, Dec. 4, 1972, Pat. No. 3,849,431.

[30] Foreign Application Priority Data

Dec. 7, 1971  Switzerland.................. 17875/71

[52] U.S. Cl. ............... 424/270; 424/180; 424/246; 424/248; 424/250; 424/267; 424/272; 424/273
[51] Int. Cl.².. A01N 9/12; A01N 9/18; A01N 9/20; A01N 9/28
[58] Field of Search ........... 424/270, 180, 246, 248, 424/250, 267, 272–273

[56] References Cited
UNITED STATES PATENTS

| | | | |
|---|---|---|---|
| 2,932,649 | 4/1960 | Metivier........................ | 260/307 D |
| 3,586,670 | 6/1971 | Brenneisen et al. ........... | 260/307 D |
| 3,720,686 | 3/1973 | Narayanan et al.............. | 260/309.2 |

Primary Examiner—Albert T. Meyers
Assistant Examiner—Allen J. Robinson
Attorney, Agent, or Firm—Harry Falber

[57] ABSTRACT

Isothiocyanobenzazoles of the formula

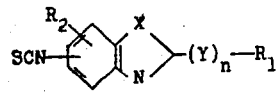

wherein
$R_1$ is hydrogen, optionally substituted alkyl, alkenyl, cycloalkyl or cycloalkenyl
$R_2$ is hydrogen, halogen, alkyl, alkoxy or alkanoyl
X is oxygen, sulfur or

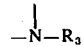

$R_3$ is hydrogen, alkyl, alkenyl, phenyl or benzyl, dialkylaminoalkyl, alkoxycarbonyl, alkanoyl or polyhydroxyalkyl
Y is oxygen, sulfur, -SO-, -SO$_2$- or

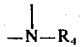

$n$ is 0 or 1, and
$R_4$ is hydrogen, alkyl or alkenyl or together with the nitrogen atom and $R_1$ a saturated or unsaturated heterocycle which may contain one further hetero atom having anthelmintic and microbicidal activity.

8 Claims, No Drawings

ANTHELMINTIC COMPOSITION AND METHOD UTILIZING ISOTHIOCYANOBENZAZOLES ACTIVE INGREDIENTS

This is a division of application Ser. No. 311,987, filed on Dec. 4, 1972, now U.S. Pat. No. 3,849,431.

The present invention relates to isothiocyanobenzazoles, to processes for the production of these new compounds, as well as to anthelmintic and microbicidal agents containing these compounds as active components.

Among the endoparasites occurring in the case of warm-blooded animals, the helminthes, in particular, cause considerable damage. For example, animals infested by worms suffer not only to the extent of retarded growth but, in some cases, to the extent of injury so severe that the animals die as a result. It is therefore of great importance that agents be developed which are suitable for the control of helminthes and of their development stages, as well as for the prevention of infestation by these parasites. By the term "helminthes" in the present description are meant nematodes, cestodes and trematodes, that is, worms of the gastrointestinal tract, of the liver and of other organs. A number of substances having anthelmintic action have indeed become known; however, these are frequently not entirely satisfactory for the given application: it may be that they have an insufficient action in compatible dosages, produce in therapeutically effective dosage levels undesired secondary effects, or have too narrow a range of action. Thus, for example, racemic 2,3,5,6-tetrahydro-6-phenyl-imidazo(2,1-5) thiazole, known from the Dutch Pat. No. 6,505,806, is effective only against nematodes, not, however, against trematodes and cestodes.

The new isothiocyanobenzazoles correspond to formula I

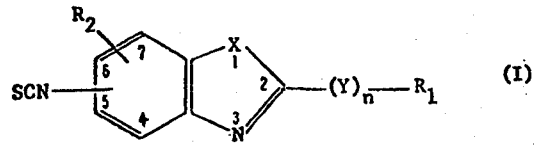

wherein the SCN-group is in the 4-, 5-, 6- or 7-position, and preferably in the 5- or 6-position, and wherein $R_1$ represents hydrogen, a straight-chain or branched alkyl or alkenyl radical having 1 to 17, preferably 1 to 5 carbon atoms, a lower alkyl or alkenyl radical having a total of at most 6 carbon atoms and substituted by halogen, -CN, -OH, alkoxy, acyl, alkylthio or dialkylamino, an optionally lower-alkyl-substituted, mono-, bi- or tricyclic cycloalkyl or cycloalkenyl radical having 3 to 10 carbon atoms in the ring structure, which can also be bound by way of a CH$_2$-group to the substituent Y or to the heterocycle, $R_2$ represents hydrogen, halogen, or an alkyl, alkoxy or acyl radical having at most 4 carbon atoms, X represents oxygen, sulphur or

$R_3$ stands for hydrogen, an alkyl or alkenyl radical having at most 5 carbon atoms, a phenyl or benzyl radical, a dimethylamino- or diethylamino-alkyl radical having 2 – 5 carbon atoms in the alkyl chain, an alkoxy-carbonyl radical having 2 – 5 carbon atoms, an aliphatic acyl radical having 2 – 5 carbon atoms, or for a polyhydroxyalkyl radical (saccharide), Y represents oxygen, sulphur, —SO—, —SO$_2$—, or

n is the number 0 to 1, $R_4$ represents hydrogen, an alkyl or alkenyl radical having at most 5 carbon atoms, or together with the N-atom and the substituent $R_1$ a saturated or unsaturated heterocycle having 4 to 6 carbon atoms which may also contain a further hetero atom O or S or the group

and $R_5$ stands for hydrogen, methyl or ethyl, and include the acid addition salts non-toxic for warm-blooded animals.

The compounds of formula 1 constitute therefore, where X = O, benzoxazole derivatives (Ia),
where X = S, benzothiazole derivatives (Ib), or
where X = —NR$_3$, benzimidazole derivatives (Ic).

The benzoxazole derivatives Ia (X = O) are able, if n = O, to convert in a reversible reaction, with the aid of strong mineral acids, into N-acylaminophenols II according to the following diagram:

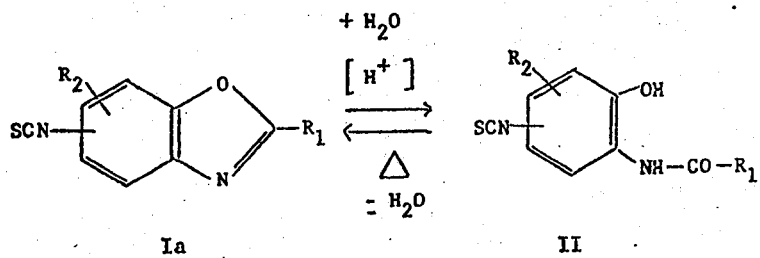

The formed N-acylaminophenols and corresponding salts likewise have anthelmintic and microbicidal activity. Their reconversion into the benzoxazole form is effected, as indicated above, by heating, with the possible addition of conventional condensing agents, e.g., phosphorus oxychloride.

The following may be mentioned as examples of straightchain or branched alkyl radicals having up to 5 carbon atoms: methyl, ethyl, n-propyl, isopropyl, n-butyl, sec.butyl, isobutyl, tert.butyl, n-amyl, sioamyl; and as examples of alkyl radicals having up to 17 carbon atoms: hexyl, 1-ethylpentyl, octyl, undecyl, dodecyl, pentadecyl and heptadecyl.

Examples of straight-chain or branched alkenyl radicals are as follows: n-propenyl, α-methylvinyl, 9-decenyl and 8-heptadecenyl.

The meaning of cycloalkyl or cycloalkenyl radicals includes also ring structures which can be substituted by methyl, ethyl, n-propyl or isopropyl. The following examples may be given: cyclopropyl, cyclobutyl, cyclopentyl, cyclohexyl, cyclohexenyl, 3,4-dimethylcyclobutyl, 2,3-dimethylcyclopropyl, 4-methylcyclohexyl, 4-isopropylcyclohexyl, 3,5-bis-(ethyl)cyclohexyl, norbornyl, norbornylmethyl, adamantyl and adamantylmethyl.

The term halogen covers fluorine, chlorine and bromine.

By polyhydroxyalkyl radicals are meant saccharide groups, particularly $C_4 - C_7$ saccharides, such as sorbose, glucose, mannose and ribose.

Saturated or unsaturated heterocycles formed from the substituents $R_1$ and $R_4$ together with the N-atom bound to them are, e.g. pyrrolidine, piperidine, 2-methylpiperidine, 4-methylpiperidine, piperazine, N'-methyl- and N'-ethyl-piperazine, morpholine, isomorpholine, thiomorpholine and hexamethyleneimine.

Suitable salts of isothiocyanobenzazoles non-toxic to warm-blooded animals are addition compounds with inorganic or organic acids, preferably fairly strong acids; examples of such acids are as follows: hydrochloric acid, hydrobromic acid, sulphuric acid, phosphoric acid, acetic acid, adipic acid, maleic acid, tartaric acid, lactic acid, citric acid, glutamic acid, aconitic acid, sulphamic acid, methanesulphonic acid and p-toluenesulphonic acid.

The compounds of formula I are highly effective against harmful bacteria and fungi, and against helminthes in all stages of development. The invention relates also to the application of compounds embraced by formula I as anthelmintics and antimicrobics.

Three important subgroups of compounds are those of formula I (benzoxazoles, benzothiazoles and benzimidazoles) and their addition salts wherein X represents oxygen, sulphur, or the group $—N(R_3)—$ defined for formula I, the SCN-group is in the 5- or 6-position, $n = O$, and $R_1$ represents a straight or branched alkyl radical having 1 to 8 carbon atoms, a propenyl, 8-heptadecenyl, heptadecyl or pentadecyl radical, or the cyclopropyl, cyclopropylmethyl, cyclobutyl, cyclopentyl or cyclohexyl radical, or wherein $n = 1$, and $—Y—R_1$ denotes a(n) hydroxyl, methoxy, ethoxy, n-propoxy, isopropoxy, mercapto, methylmercapto, ethylmercapto, n-propylmercapto, isopropylmarcapto, n-butylmercapto, methylsulphonyl or ethylsulphonyl, or a mono- or dialkylamino radical having at most 6 carbon atoms, and $R_2$ represents hydrogen, a chlorine or bromine atom, a methyl, methoxy or acetyl group.

The following compounds have proved particularly good active substances:

2-[n-amyl]-6-isothiocyanobenzothiazole,
2-isopropyl-6-isothiocyanobenzothiazole,
2-methyl-6-isothiocyanobenzothiazole,
2-ethyl-6-isothiocyanobenzothiazole,
2-[n-propyl]-6-isothiocyanobenzothiazole,
2-[n-amyl]-5-isothiocyanobenzothiazole,
2-[n-propyl]-5-isothiocyanobenzothiazole,
2-isopropyl-5-isothiocyanobenzothiazole,
2-ethyl-5-isothiocyanobenzothiazole,
2-[n-amyl]-6-isothiocyanobenzoxazole,
2-isopropyl-6-isothiocyanobenzoxazole,
2-ethyl-6-isothiocyanobenzoxazole,
2-tert.butyl-6-isothiocyanobenzoxazole,
2-cyclopropyl-6-isothiocyanobenzothiazole,
2-[n-amyl]-5-isothiocyanobenzoxazole,
2-isopropyl-5-isothiocyanobenzoxazole,
2-ethyl-5-isothiocyanobenzoxazole,
2-n-octyl-5-isothiocyanobenzoxazole,
2-ethoxy-6-isothiocyanobenzoxazole,
2-mercapto-6-isothiocyanobenzoxazole,
2-methylthio-5-isothiocyanobenzoxazole,
2-isopropylthio-5-isothiocyanobenzoxazole,
2-n-butylthio-6-isothiocyanobenzoxazole,
2-methylthio-6-isothiocyanobenzoxazole,
2-methoxy-6-isothiocyanobenzothiazole,
2-hydroxy-6-isothiocyanobenzothiazole,
2-isopropoxy-6-isothiocyanobenzothiazole,
2-methylthio-6-isothiocyanobenzothiazole,
2-ethylthio-6-isothiocyanobenzothiazole,
2-methylsulphonyl-6-isothiocyanobenzothiazole,
2-mercapto-6-isothiocyanobenzothiazole,
2-n-propylthio-5-(6)isothiocyanobenzimidazole,
5(6)-chloro-6(5)isothiocyano-1-methoxycarbonyl-2-n-propylbenzimidazole,
5(6)-isothiocyano-1-ethyl-2-methylbenzimidazole.

The new active substances of formula I according to the invention are suitable for the control of parasitic nematodes of the orders:

Dracunculoidia,
Ascaroidea (e.g., *Ascaridia galli*),
Trichenelloidea,
Strongyloidea,
Trichostrongyloidea,
Metastrongyloidea, or for the control of cestodes of the families:

Dilepididae (e.g., *Hymenolepis nana*,
Taeniidae,
Diphyllobotridae, or for the control of trematodes of the families:

Dicrocoelidae,
Fasciolidae (e.g. *Fasciola hepatica*),
Schistosamatidae (e.g. *Schistosoma bovis*), in the case of domestic and useful animals, such as cattle, sheep, goats, horses, pigs, cats, dogs, as well as poultry. The new active substances can be administered in single doses to the animals, or in repeated doses, the single doses preferably being, depending on the species of animal, between 25 to 1,000 mg per kilogram of body weight. A better effect can be obtained in some cases by a protracted administration of the active substances, or smaller total doses may suffice to obtain the desired effect. The active substances or mixtures containing them can also be added to the feed or to the drinking water. The finished feed contains the substances of formula I preferably in a concentration of ca. 0.05 to 1.0 per cent by weight.

The new active substances can be administered as agents orally or abomasally to the animals, the said agents being, for example, in the form of solutions, emulsions, suspensions (drenches), powders, tablets, boluses, and capsules. The usual solid carriers are used to produce the above mentioned preparations, such as, for example, kaolin, talcum, bentonite, sodium chloride, calcium phosphate, carbohydrates, cellulose powder, cottonseed meal, Carbowaxes, and gelatine, or liquids such as water, optionally with the addition of surface-active substances such as ionic or non-ionic dispersing agents, as well as oils, and other solvents and diluents harmless to the animal organism. If the anthelmintic agents are in the form of feed concentrates, then the carriers used are, for example, production feed, fodder grain or protein concentrates. Such feed concentrates or agents can contain, in addition to the active substances, also additives, vitamins, antibiotics, chemotherapeutical agents, or other pesticides, chiefly bacteriostatics, fungistatics, coccidiostatics, also hormone preparations, substances having anabolic activity, or other substances promoting growth, affecting the quality of the meat of slaughter cattle, or in some other way beneficial for the organism.

For combination with the active substances according to the invention, it is possible to use, for example, the following anthelmintics:

Principally as nematocides

Absonal
Alcopar
Anthelcide
Ascaridole
Badminth II
Bephenium
Bradosol
Cambendazol
Chlorophos
Chlorthion
Coumaphos
Cyanin
Destomycin
Diethylcarbamazine
Dichlorophene,
DDVP
1,4-di-(D-glucosyl)-piperazine
Dithiazonine
Dow ET/70
Dowco 132
Dymanthine . HCl
Egressin
Gainex
Hexachlorophene
Hexylresorcinol
Ionit
Levamisol
Mepacrine
Methylene violet
1-Methyl-1-tridecylpiperazinium-4-carboxylic acid ethyl ester
Methyridine
Monopar
Narlene
Neguvon
Nematodin
Nemural
Mebendazol
Nidanthel
Parbendazol
Parvex
Phenothiazine
Piperazine
Polymethylene-piperazine
Promethazine
Pyrantel
Pyrathiazine
Pyryinium-embonate
Rametin
Ronnel
Santonin
Shell 1808
Stilbazium
Tetramisole
Thenium
Thiabendazole
Thymolan
Triclofenol
Treclofenol-piperazine
Vermella
Principally as trematocides:
Acedist
Bilevon M
Bilevon R
Bithionol
Disophenol
Freon 112
Hetol
Hetolin
Hexachloroethane
Hexachlorophene
Hilomid
Niclofolan
Nitroxynil
Ranide
Tremerad
Tribromsalan (Tremasept II)
Zanil
Brotianid
Principally as cestocides:
Acranil
Arecoline
Atebrin
Bithionol
Bithionol oxide
Bunamidine
Cestodin
Cambendazol
Dibutyltin dilaurate
Dichlorophen
Dioctyltin dichloride
Dioctyl tin laurate
Doda
Filixic acid
Hexachlorophene
Nidanthel
Terenol
Yomesan For combination with the active substances according to the invention, it is also possible to use preparations containing several active substances, e.g.:

| | |
|---|---|
| Eludon | Piperazine-hexahydrate + Copper sulphate + Sodium metaarsenite |
| Equizol A | Thiabendazole + Piperazine phosphate |
| Nilzan | Tetramisole + Zanil |
| Nitroarene | Yomesan + Dichlorophene |
| Parvec plus | Phenothiazine + Piperazine-CS$_2$-complex |
| Phenovis 2 | Phenylbenzimidazole + Phenothiazine |

Microbicidal agents according to the invention are produced in a manner known per se by the intimate mixing and grinding of active substances of the general formula I with suitable carriers, optionally with the addition of dispersing agents or solvents which are inert to the active substances. The active substances can be obtained and used in the forms described below, the given information applying in some cases also to the production of anthelmintic agents:

solid preparations: dusts, scattering agents, granulates, (coated granulates, impregnated granulates and homogeneous granulates);

water-dispersible concentrates of the active substance: wettable powders, pastes, emulsions;
liquid preparations: solutions.

The solid preparations (dusts, scattering agents, granulates) are produced by the mixing of the active substances with solid carriers. Suitable carriers are, e.g., kaolin, talcum, bole, loess, chalk, limestone, ground limestone, dolomite, diatomaceous earth, precipitated silicic acid, alkaline-earth silicates, sodium and potassium aluminium silicates (feldspar and mica), calcium and magnesium sulphates, ground synthetic materials, ground vegetable products such as bran, bark dust, sawdust, ground nutshells, cellulose powder, residues of plant extractions, active charcoal, etc., alone or in admixture with each other.

The particle size of the carriers is for dusts advantageously up to about 0.1 mm; for scattering agents from about 0.075 mm to 0.2 mm; and for granulates 0.2 mm or coarser.

The concentrations of active substance in the solid preparation forms are from 0.5 to 80%.

To these mixtures may also be added additives stabilising the active substance, and/or non-ionic, anion-active, and cation-active substances, which, for example, improve the adhesiveness of the active substances (adhesives and agglutinants), and/or ensure a better wettability (wetting agents) and dispersibility (dispersing agents). Suitable adhesives are, for example, the following: olein/lime mixture, cellulose derivatives (methyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acids, their alkali metal and alkaline-earth metal salts, polyethylene glycol ethers (Carbowaxes), fatty alcohol polyethylene glycol ethers having 5 to 20 ethylene oxide radicals per molecule and 8 to 18 carbon atoms in the fatty alcohol moiety, condesation products of ethylene oxide, propylene oxide, polyvinyl pyrrolidones, polyvinyl alcohols, condensation products of urea and formaldehyde, as well as latex products.

Water-dispersible concentrates of active substance, i.e., wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents. The concentration of active substance in these agents is 5 to 80%.

The wettable powders and the pastes are obtained by the mixing and grinding of the active substances with dispersing agents and pulverulent carriers, in suitable devices, until homogeneity is attained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylaryl sulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ether, the sodium salt of oleyl ethionate, the sodium salt of oleyl methyl tauride, ditertiary acetylene glycols, dialkyl dilauryl ammonium chloride, and fatty acid alkali-metal and alkaline-earth metal salts.

Suitable anti-foam agents are, for example, silicones.

The active substances are so mixed, ground sieved and strained with the above mentioned additives that the solid constituent in the case of wettable powders has a particle size not exceeding 0.02 to 0.04 mm, and in the case of pastes not exceeding 0.03 mm. Dispersing agents such as those mentioned in the preceding paragraphs, organic solvents and water are used in the preparation of emulsion concentrates and pastes. Suitable solvents are, e.g., the following: alcohols, benzene, xylenes, toluene, dimethylsulphoxide, and mineral oil fractions boiling in the range of 120° to 350°C. The solvents must be practically odourless, non-phytotoxic, inert to the active substances, and not readily inflammable.

Furthermore, the agents according to the invention can be used in the form of solutions. For this purpose the active substance (or several active substances) of the general formula I is (or are) dissolved in suitable organic solvents, mixtures of solvents, or water. As organic solvents it is possible to use aliphatic and aromatic hydrocarbons, their chlorinated derivatives, alkylnaphthalenes, mineral oils on their own or in admixture with each other. The solutions should contain the active substances in a concentration of from 1 to 20%.

Other biocidal active substances, such as pesticides, may by added to the described agents according to the invention. For the widening of their sphere of action, the new agents may also contain, in addition to the stated compounds of formula I, e.g. fungicides, bactericides, fungistatics, bacteriostatics or nematocides, or other active substances.

Isothiocyanobenzazoles of formula I can be produced according to the invention by a process in which the basic aminobenzazoles of formula III

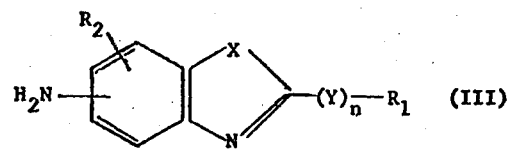

| | |
|---|---|
| IIIa : | X = O |
| IIIb : | X = S |
| IIIc : | X = —NR$_3$ | are
a. reacted with a thiocarbonic acid derivative of the formula

wherein Hal represents chlorine or bromine, and Y represents chlorine, bromine or a dialkylamino group; or b. reacted with a sulphide of the formula

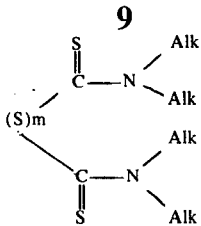

wherein Alk denotes a lower alkyl radical having at most four carbon atoms; or c. reacted with pentathio-dipercarbonic acid-bis-(trihalogen-alkyl)-esters; or
d. reacted with phosgene and phosphorus pentasulphide in a solvent or diluent inert to the reactants; or
e. converted with benzoylisothiocyanate into the corresponding thiourea, and this thermally decomposed in the presence of a solvent inert to the reactants, preferably in an aromatic hydrocarbon or halogenated hydrocarbon, or in the presence of acids or acid anhydrides; or
f. converted with carbon disulphide in the presence of an inorganic base, or of an amine, into the corresponding dithiocarbamic acid salts, and these then dehydrosulphated; or
g. reacted with carbon disulphide in the presence of carbodiimides and of a tertiary amine; or
h. reacted with ammonium rhodanide in the presence of gaseous hydrogen chloride.

The processes are performed in solvents or diluents which are inert to the reactants.

The following, for example, can be used in the procfess according to the invention:
aliphatic and aromatic hydrocarbons, aliphatic and aromatic halogenated hydrocarbons, ethers and ethereal
compounds such as dioxane or tetrahydrofuran, ketones,
amides such as dimethylformamide, etc., water, or mixtures of such solvents with water.

In the preparation of isothiocyano compounds of formula I by the methods given under (a) – h), temperatures of between −20° and +100°C are maintained, preferably of between −10° and +30°C, and with application of a dialkylthiocarbamoyl halide such as diethylthiocarbamoyl chloride, or in the case of thermal decomposition according to method e), higher temperatures of between 40° and 200°C are used.

The formation of the isothiocyano group involves known methods: reactions of amines with thiophosgene (a) are described in Houben-Weyl, 4th edition, Vol.9, p. 876 (1955), the use of acid-binding agents by O. E. Schultz in Arch. Pharm. 295, 146–151 (1962); the reaction of amines with N,N-diethylthiocarbamoyl chloride (a) has been described in Journal org. Chem. 30, 2465 (1965), that with bis-thiocarbamoyl sulphides (b) by F. H. Marquardt in Helv. chim. Acta 49, 1716 (1966), and that with pentathiodipercarbonic acid-bis-(trihalogenoalkyl)-ester (c) by R. Gottfried in Angew. Chem. 78, 985 (1966), and that with phosgene and phosphorus pentasulphide according to Horben-Weyl 4th edition, Vol. 9, p. 867 ff.

The preferred solvents for the reactions given under (d) and (e) are o-dichlorobenzene and chlorobenzene; other dichlorobenzenes, toluene, xylenes, cumol, etc. are however also suitable. The thermal decomposition of thioureas (e) is performed in the manner described by J. N. Baxter et.al. in J. Chem. Soc. (1956), p. 659 ff.

The thioureas are produced according to Org. Syntheses III, 735, (1955). The inorganic bases used in the production of dithiocarbamic acid salts (f) are, e.g., the hydroxides, oxides and carbonates of alkali and alkaline-earth metals, as well as ammonium hydroxide; and the amines used are, e.g. trialkylamines, pyridine bases or ammonia (cp. C.A. 70, 3389 q (1969)). Dehydrosulphuration (c) can be carried out oxidatively with metal salts (Brit. Pat. No. 793,802, Dutch Patent No. 81,326), e.g. with lead, copper, zinc or iron-III salts, iodine, alkali metal hypochlorites and -chlorites, preferably with those of potassium and sodium (French Patent No. 1,311,855), also with suitable acid halides such as phosgene and phosphorus oxychloride (D. Martin et.al. Chem. Ber. 98, 2425–2426 (1965)), as well as with elementary chlorine and ammonium sulphide (DAS 1,192,139) or chloramine T (British Patent. No 1,024,913).

Isothiocyanobenzazoles of formula I can be prepared, for example, by the reaction of aminobenzazoles, which can be obtained from nitrobenzazoles in the usual manner by reduction with zinc, iron or $SnCl_2$ in acid solution, with catalytically activated hydrogen, or with sodium borohydride, with thiophosgene in mineral acids, preferably concentrated hydrochloric acid, according to:

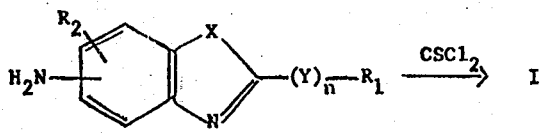

III

The reaction with $CSCl_2$ can however also be smoothly performed in the presence of an acid-binding agent such as an organic base, e.g., triethylamine, pyridine, N,N-dimethylaniline, or of an inorganic weak base such as $CaCO_3$, $BaCO_3$, Na-acetate, $NaHCO_3$, $KH_2PO_4$. This variant will be advantageously used in the case of the hydrolysissensitive conversion of an aminobenzoxazole into isothiocyanobenzoxazole, in order to avoid the benzoxazole-ring-opening according to Ia → II, which would have to be subsequently reclosed, if at all possible, by heating in a further stage of the process.

On the other hand, this reaction behaviour can for a number of isothiocyanobenzoxazoles be made the basis of a further production process. Those compounds of formula Ia wherein $n = 0$ can be obtained from the basic aminoacylaminophenols of formula IV (with $R_6 =$ H or $—CO—R_1$) by reaction with thiophosgene (or with one of the other reagents given under the methods (a) to (h), and subsequent ring condensation according to:

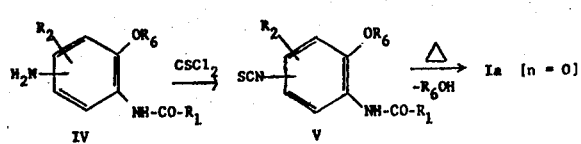

IV    V

Salts of isothiocyanobenzoxazoles Ia can be produced, on account of hydrolysis sensitivity, practically only with weak acids, preferably organic acids. On the other hand, salts of benzothiazoles Ib, or of benzimidazoles Ic, can be prepared with either strong or weak acids. The hydrochlorides of these two last-mentioned subgroups can also be obtained direct from amino compounds of formulae IIIb or IIIc if thiophosgene is used for the reaction in anhydrous solvents, or in mineral acids such as hydrochloric acid or sulphuric acid.

Aminobenzoxazoles of formula IIIa and their immediate precursors, the nitrobenzoxazoles, are in some cases known, or can be produced by known methods [cp. M. A. Phillips, J. Chem. Soc. 1928, 122; ibid. 1930, 2685-2730; I. K. Ushenko, Zh. obsc. Ch. 30, 2658-69 (1960); A. Cerniani and R. Passerini, Ann. Chim. (Roma) 44, 3–10 (1954)].

The ring closure of a N-acylated or N,O-bisacylated o-aminophenol to the corresponding benzoxazole by simple distillation with the splitting off of water, as corresponds also to the reaction behaviour of the compounds II or V with conversion into Ia, is described by F. M. Hamer, J. Chem. Soc. 1956, 1480. The reaction can by advantageously performed also with condensation agents such as $ZnCl_2$, $POCl_3$, $P_2O_5$ or $H_3BO_3$ [cp. M. A. Phillips, J. Chem. Soc. 1928, 121; U.S. Pat. 3,158,610]. The use of $H_3BO_3$ is particularly favourable and reduces the risk of the formation of resinification products.

Aminobenzothiazoles of formula IIIb and their precursors, the nitrobenzothiazoles, are in some cases likewise known, or can be produced by known methods. (cp. Beilstein's Handbuch der organischen Chemie [Handbook of Organic Chemistry] 27, p. 47; ibid. 27, II, 427; Chemical Abstracts 48, 2689d; ibid. 49, 6232b; ibid. 49, 11625b; ibid. 57, 13925a; ibid. 69, 10032; ibid. 70, 57724; I. K. Ushenko, Zh. obsc. Ch. 30, 2658-69 [1960]; British Pat. No. 913,910 [1962]; French Pat. No. 1,379,470 (1964); British Pat. No. 598,985 (1948); T. Takahashi and J. Okada, J. Pharm. Soc. Japan 75, 277-280 [1953]).

Aminobenzimidazoles of formula IIIc as well as their precursores, nitrobenzimidazoles, are in some cases known, or can be produced by known methods. (O. Kym, J.prakt. Ch. 75, 323 [1907]; A. Ricci, Gazz. Chim. Ital. 97, 741–749, 758-768 [1967]; Shotaro Nakajima et al., Yakugaku Zasshi 78, 1378-1382 [1958]).

A general method for the production of most of the starting compounds III comprises the conversion of 2-thiolbenzazoles by chlorination into 2-chlorobenzazoles, and the introduction of the groups $-OR_1$ or $-N(R_1)(R_4)$ with the aid of a corresponding alcoholate or sec. amine; or, for the introduction of the group $-S-R_1$, the reaction of the basic 2-thiolbenzazole direct with a halide $Hal-R_1$. The substituents $O_2N-$ and $R_2$ can be thereby introduced, at a point of time appearing suitable, before or after this production process. An oxidation, performed before introduction of the isothiocyano group, with, e.g., $NaOH/H_2O_2$, converts the group $-S-R_1$ into $-S-R_1$ into $-SO-R_1$ or $-SO_2 13 R_1$.

In the case n = 0 of the direct bond of $R_1$ to the heterocyclic ring, it is preferable to commence with a corresponding ortho-substituted aniline (as has already been indicated with respect to the production of benzooxazoles in the conversion IV → Ia), in that a corresponding o-aminothiophenol undergoes the ring closure reaction with, e.g., an acid halide $Hal-CO-R_1$ or an acid anhydride $O(COR_1)_2$ to give benzothiazole; or in that a corresponding o-phenylenediamine bisacylated by $-CO-R_1$ is condensed to benzimidazole; or in that, e.g. an o-phenylenediamine substituted by $R_2$ is reacted with urea to give 2-hydroxybenzimidazole, which can be chlorinated with $POCl_3$ in the 2-position, and thereupon nitrated in the condensed benzene ring.

EXAMPLE 1

Production of 2-[n-amyl]-6-isothiocyano-benzoxazole (compound No. 1.9)

a. An amount of 188 g of crude 5-nitro-2-caproylaminophenol is heated with 46 g of boric acid with elimination of water, until the internal temperature has attained 210–220°C. The mixture is then cooled, stirred with chloroform and filtered. The filtrate is repeatedly washed with water, dried, and the solvent removed. The 2-[n-amyl]-6-nitro-benzoxazole remaining boils at 128–132°C (0.1 Torr).

b. An amount of 122 g of 2-[n-amyl]-6-nitro-benzoxazole is dissolved in 1500 ml of distilled anhydrous ethanol, and, after the addition of 15 g of Raney nickel at room temperature to slightly elevated temperature (below 55°C), hydrogenated. Raney-nickel is filtered of under suction, the filtrate separated from the ethanol, and the residue remaining recrystallised from cyclohexane to obtain 2-[n-amyl]-6-amino-benzoxazole, M.P. 57°–59°C.

c. An amount of 40.8 g of 2-[n-amyl]-6-amino-benzoxazole is dissolved in 370 ml of anhydrous acetone. After the addition of 50 g of powdered anhydrous $CaCO_3$, the mixture is cooled to 0°C, and at this temperature an addition made dropwise, with stirring, of a solution of 29.7 g of $CSCl_2$ in 30 ml of anhydrous acetone. The mixture is then stirred at 0° to 5°C for 5 hours and filtered. After concentration of the filtrate at 30°C in a slight vacuum, the residue is recrystallised from petroleum ether to obtain 2-[n-amyl]-6-isothiocyano-benzoxazole, M.P. 31–34°C

EXAMPLE 2

Production of 2-[n-amyl]-6-isothiocyano-benzoxazole (Comp. No. 1.9)

a. An amount of 22 g of 2-caproylamido-5-nitrophenol is dissolved under nitrogen in 500 ml of distilled dioxane, and, after the addition of 8 g of Raney-nickel, hydrogenated at room temperature or at 30°–40°C until the reaction is complete. Raney-nickel is filtered off under suction. The obtained filtrate with the contained 2-caproylamido-5-aminophenol can be used direct for the subsequent thiophosgenation. It is also possible to firstly isolate the intermediate by removal of the dioxane by distillation.

b. An amount of 50 ml of conc. hydrochloric acid is added at 0° to 5°C, with stirring, to a solution of 18 g of 2-caproylamido-5-aminophenol in 300 ml of water. There is then added dropwise to this mixture, in the course of 20 minutes, 14 g of $CSCl_2$; the whole is subsequently stirred for 12 hours at 5°C, and the final product dried; it melts, after recrystallisation from benzene, at 148°–150°C.

c. The obtained 2-caproylamido-5-isothiocyanophenol can be cyclised in an $N_2$-stream by rapid heating at ca. 210°C, in the presence of boric acid, for 15 minutes with elimination of water to give 2-[n-amyl]-6-isothiocyanobenzoxazole, which can be obtained by the addition of petroleum ether and subsequent cooling.

EXAMPLE 3

Production of 2-methyl-6-isothiocyano-benzoxazole (Compound No. 1.2)

An amount of 10.4 g of 2-acetamido-5-isothiocyanophenol, which was obtained by thiophosgenation from 2-acetamido-5-aminophenol, is heated with 3.4 g of boric acid for 15 minutes at 200°C, and then immediately cooled. The residue is extracted with hot cyclohexane; the solution is concentrated by evaporation, cooled and petroleum ether added, whereby the desired final product crystallises out, M.P. 68°–70°C.

It is possible to produce in an identical manner to that described in Examples 1 to 3, or by a corresponding method previously described, the following isothiocyanobenzoxazoles of formula Ia, from which corresponding acid addition salts are obtainable:

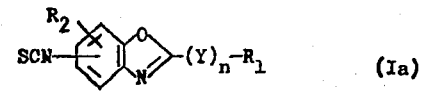

(Ia)

| (n=0) Compound No. | SCN— position | $R_2$ | $R_1$ | Physical data |
|---|---|---|---|---|
| 1.1 | 6 | H | H | |
| 1.2 | 6 | H | $CH_3$ | M.P. 68–70°C |
| 1.3 | 6 | H | $C_2H_5$ | M.P. 64–68°C |
| 1.4 | 6 | H | n—$C_3H_7$ | |
| 1.5 | 6 | H | iso—$C_3H_7$ | |
| 1.6 | 6 | H | n—$C_4H_9$ | |
| 1.7 | 6 | H | iso—$C_4H_9$ | |
| 1.8 | 6 | H | tert.—$C_4H_9$ | M.P. 77–79°C |
| 1.9 | 6 | H | n—$C_5H_{11}$ | M.P. 31–34°C |
| 1.10 | 6 | H | N-Octyl | M.P. 41–42°C |
| 1.11 | 6 | H | 8-Heptadecenyl | $n_D^{20}$ 1.5498 |
| 1.12 | 6 | H | —CH=CH—$CH_3$ | |
| 1.13 | 6 | H | Cyclopropyl | |
| 1.14 | 6 | H | 2,3-Dimethyl-cyclopropyl | |
| 1.15 | 4 | H | $CH_3$ | |
| 1.16 | 7 | H | $CH_3$ | |
| 1.17 | 5 | H | $CH_3$ | M.P. 82–84°C |
| 1.18 | 5 | H | $C_2H_5$ | M.P. 43–48°C |
| 1.19 | 5 | H | n—$C_3H_7$ | |
| 1.20 | 5 | H | iso—$C_3H_7$ | |
| 1.21 | 5 | H | n—$C_4H_9$ | |
| 1.22 | 5 | H | iso—$C_4H_9$ | M.P. 49–51°C |
| 1.23 | 4 | H | n—$C_5H_{11}$ | |
| 1.24 | 7 | H | n—$C_5H_{11}$ | |
| 1.25 | 5 | H | tert.—$C_4H_9$ | |
| 1.26 | 5 | H | n—$C_5H_{11}$ | |
| 1.27 | 5 | H | Heptadecyl | M.P. 65–70°C |
| 1.28 | 5 | H | —C=$CH_2$<br>\|<br>$CH_3$ | |
| 1.29 | 5 | H | Cyclopropyl | |
| 1.30 | 5 | H | Cyclohexyl | M.P. 72–73°C |
| 1.31 | 6 | 5—$C_2H_5O$— | —CH($C_2H_5$)$_2$ | |
| 1.32 | 6 | 5-tert.$C_4H_9$ | —⟨⟩ | |
| 1.33 | 7 | H | iso-$C_3H_7$ | |
| 1.34 | 7 | 5—Cl | $CH_3$ | |
| 1.35 | 7 | 5—$CH_3$ | $CH_3$ | |
| 1.36 | 5 | 7—Cl | $CH_3$ | |
| 1.37 | 5 | 7—Br | $CH_3$ | |
| 1.38 | 6 | 5—Cl | —n—$C_{15}H_{31}$ | |
| 1.39 | 6 | 5—$CH_3$ | $CH_3$ | |
| 1.40 | 5 | 6—$CH_3O$ | $CH_3$ | |
| 1.41 | 5 | 6—$CH_3O$ | iso-$C_3H_7$ | |
| 1.42 | 7 | H | H | |
| 1.43 | 6 | 5—Cl | —n—$C_5H_{11}$ | |
| 1.44 | 4 | H | H | |
| 1.45 | 4 | H | $CH_3$ | |
| 1.46 | 6 | 5—$CH_3$ | —$CF_3$ | M.P. 82–83°C |
| 1.47 | 6 | 5—$CH_3$ | —CH($C_2H_5$)—n$C_4H_9$ | 151–153°C/0,2 Torr. | as well as compounds of formula Ia with n=1

| Compound No. | SCN— position | $R_2$ | Y | $R_1$ | Physical data |
|---|---|---|---|---|---|
| 1.48 | 6 | H | S | H | M.P. 258–261°C |
| 1.49 | 6 | H | S | $CH_3$ | M.P. 86–91°C |
| 1.50 | 6 | H | S | —n—$C_4H_9$ | M.P. 50°C |
| 1.51 | 5 | H | S | H | M.P. 250–256°C |
| 1.52 | 5 | H | S | $CH_3$ | M.P. 136–138°C |
| 1.53 | 5 | H | S | iso—$C_3H_7$ | M.P. 65–67°C |
| 1.54 | 5 | H | S | —n—$C_5H_{11}$ | |
| 1.55 | 5 | H | S | —$CH_2$—⟨ | |
| 1.56 | 5 | H | S | —$CH_2$—S—$CH_3$ | |
| 1.57 | 6 | 5—$CH_3$ | S | —$CH_2$—$CH_2$—CH($CH_3$)$_2$ | |
| 1.58 | 6 | 5—Cl | S | Cyclopentyl | |
| 1.59 | 6 | H | S | Cyclohexyl | M.P. 72–75°C |
| 1.60 | 6 | H | S | —n—$C_{12}H_{25}$ | M.P. 50–51°C |

-continued

| Compound No. | SCN— position | $R_2$ | Y | $R_1$ | Physical data |
|---|---|---|---|---|---|
| 1.61 | 6 | H | S | $-CH_2-CH=CH_2$ | |
| 1.62 | 6 | H | $-N(CH_3)-$ | $CH_3$ | |
| 1.63 | 6 | H | $-N(C_2H_5)-$ | $C_2H_5$ | M.P. 56–57°C |
| 1.64 | 6 | H | $-N(C_2H_5)-$ | $C_2H_5$(hydrochloride) | M.P. 110°C |
| 1.65 | 6 | H | $-N-C_4H_{9-n}$ | $n-C_4H_9$ | $n_D^{20}$ 1.6205 |
| 1.66 | 6 | H | $-N-C_4H_{9-n}$ | $n-C_4H_9$ (hydrochloride) | M.P. 92°C |
| 1.67 | 6 | H | -N◯ (pyrrolidine) | | |
| 1.68 | 6 | H | -N◯ (piperidine) | | M.P. 81–83°C |
| 1.69 | 6 | H | -N◯ (morpholine) | | |
| 1.70 | 6 | H | -N◯N—$CH_3$ | | M.P. 119–120°C |
| 1.71 | 6 | H | -N◯($CH_2$)$_6$ | | |
| 1.72 | 6 | H | O | $-C_2H_5$ | M.P. 70–76°C |
| 1.73 | 6 | H | O | H | |
| 1.74 | 5 | H | O | H | |
| 1.75 | 5 | H | O | $-C_3H_7n$ | |
| 1.76 | 6 | H | O | iso—$C_3H_7$ | |
| 1.77 | 6 | H | O | $-CH_2CH_2OC_2H_5$ | |
| 1.78 | 6 | 5—Cl | O | $-n-C_4H_9$ | |
| 1.79 | 6 | 5—$CH_3$ | O | iso—$C_3H_7$ | |
| 1.80 | 6 | 5—$CH_3$ | -N◯N—$CH_3$ | | |

EXAMPLE 4

Production of 2-isopropyl-6-isothiocyano-benzothiazole

An amount of 19.2 g of crude 2-isopropyl-6-aminobenzothiazole obtained by catalytic hydrogenation is dissolved in 150 ml of acetone; a mixture of 8.5 ml of concentrated hydrochloric acid and 70 ml of water is then added and the solution cooled to 5°C. In the course of half an hour, a solution of 15 g of thiophosgene in 10 ml of acetone is added dropwise, and the whole stirred for 4 hours at 10°C. The solution is allowed to stand overnight at room temperature; it is then poured into 1,000 ml of water, and the formed precipitate separated by filtration under suction. There is obtained, after recrystallisation, the pure final product of the formula

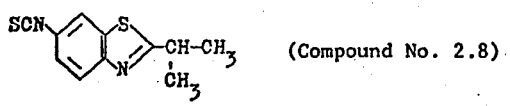 (Compound No. 2.8)

M.P. 52°–54°C

EXAMPLE 5

Production of 2-ethyl-6-isothiocyano-benzothiazole (Compound No. 2.6)

a. An amount of 15 g of thiophosgene (dissolved in 10 ml of acetone) is added dropwise in the course of 20 minutes at 5°–10°C, with stirring, to a solution of 17.8 g of 2-ethyl-6-amino-benzothiazole, 150 ml of acetone, 8.4 ml of conc. hydrochloric acid and 50 ml of water. After 4 hours' stirring, the solution is allowed to stand for ten hours at room temperature; it is then filtered and concentrated in vacuo (water-jet vacuum). The residue recrystallised from dioxane is 2-ethyl-6-isothiocyanobenzothiazole-hydrochloride, M.P. 116°–120°C.

From the dioxane filtrate, the residue obtained by concentration by evaporation is recrystallised from cyclhexane, and the free base 2-ethyl-6-isothiocyanobenzothiazole, M.P. 69°–73°C, is obtained, from which, by dissolving in anhydrous dioxane and introduction of HCl-gas at 10°, likewise the hydrochloride is formed, which is obtained as precipitate, M.P. 116°–120°C.

b. An amount of 13 g of 2-ethyl-6-isothiocyano-benzothiazole-hydrochloride is stirred with 100 ml of chloroform and 100 ml of saturated sodium carbonate solution for 15 minutes at 10°C. The chloroform is then separated, washed with water, dried with Mg-sulphate, and concentrated by evaporation. There is obtained, after recrystallisation of the residue from ligroin/petroleum ether, as pure final product the compound of the formula

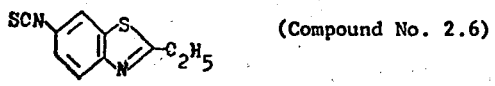 (Compound No. 2.6)

M.P. 69°–73°C.

It is possible to obtain in the same manner as that described in Examples 4 and 5, or by one of the methods previously indicated, the following isothiocyanobenzothiazoles of formula Ib

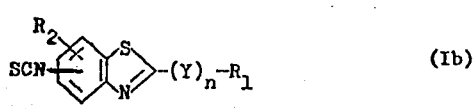 (Ib)

($n = O$) from which corresponding acid addition salts are obtainable:

| Compound No. | SCN-position | R₂ | R₁ | Physical data |
|---|---|---|---|---|
| 2.1 | 4 | H | H | M.P. 120–122°C |
| 2.2 | 4 | H | C₂H₅ | |
| 2.3 | 7 | H | C₂H₅ | |
| 2.4 | 6 | H | H | M.P. 125°C |
| 2.5 | 6 | H | CH₃ | M.P. 118–120°C |
| 2.6 | 6 | H | C₂H₅ | M.P. 69–73°C |
| 2.7 | 6 | H | —n—C₃H₇ | M.P. 60–62°C |
| 2.8 | 6 | H | iso—C₃H₇ | M.P. 52–54°C |
| 2.9 | 6 | H | sec—C₄H₉ | B.P.₀.₀₆ 142°C |
| 2.10 | 6 | H | tert.—C₄H₉ | M.P. 87–90°C |
| 2.11 | 6 | H | —n—C₅H₁₁ | M.P. 75–77°C |
| 2.12 | 6 | H | iso—C₅H₁₁ | |
| 2.13 | 6 | H | —n—C₈H₁₇ | |
| 2.14 | 6 | H | —n—C₁₁H₂₃ | M.P. 51–53°C |
| 2.15 | 6 | H | —CH—C₄H₉n<br>\|<br>C₂H₅ | |
| 2.16 | 6 | H | —C=CH₂<br>\|<br>CH₃ | |
| 2.17 | 6 | H | —CH₂—CH=CH—CH₃ | |
| 2.18 | 6 | H | Cyclopropyl | |
| 2.19 | 6 | H | Cyclopentyl | |
| 2.20 | 6 | H | Cyclohexyl | |
| 2.21 | 5 | H | Isopropyl | M.P. 34–36°C |
| 2.22 | 6 | 4—Cl | CH₃ | |
| 2.22 | 6 | 7—Cl | CH₃ | |
| 2.23 | 6 | 5—CH₃ | CH₃ | |
| 2.24 | 6 | 5—CH₃O— | CH₃ | |
| 2.25 | 5 | 6—C₂H₅ | CH₃ | |
| 2.26 | 5 | 4—C₂H₅ | —n—C₅H₁₁ | |
| 2.27 | 5 | 6—CH₃O | —n—C₅H₁₁ | |
| 2.28 | 5 | 6—CH₃O |  | |
| 2.29 | 6 | 4—Cl |  | |
| 2.30 | 6 | H | 3-Chloropropyl | |
| 2.31 | 7 | 6—CH₃O | C₂H₅ | |
| 2.32 | 6 | 5-tert.C₄H₉ | CH₃ | |
| 2.33 | 5 | 4—Cl | CH₃ | |
| 2.34 | 6 | H | CF₃ | |
| 2.35 | 6 | H | CCl₃ | |
| 2.36 | 4 | H | CH₃ | |
| 2.37 | 7 | H | CH₃ | |
| 2.38 | 7 | H | H | |
| 2.39 | 7 | H | —n—C₅H₁₁ | |
| 2.40 | 4 | H | —n—C₅H₁₁ | |
| 2.41 | 4 | 6—C₂H₅O— | —n—C₃H₇ | |
| 2.42 | 6 | H | Bicyclo-[2,2,1]-hept-5-en-2-ylmethoxy | |
| 2.43 | 6 | H | Bornyloxy | | as well as following compounds of formula Ib with n=1:

| Compound No | SCN-position | R₂ | Y | R₁ | Physical data |
|---|---|---|---|---|---|
| 2.44 | 6 | H | S | sec.C₄H₉ | |
| 2.45 | 6 | H | —SO₂— | sec.C₄H₉ | |
| 2.46 | 6 | H | O | Adamantylmethyl | |
| 2.47 | 6 | 5—Cl | S | —C₂H₄—S—C₃H₇ | |
| 2.48 | 5 | 6—CH₃ | S | —C₂H₄—O—C₂H₅ | |
| 2.49 | 6 | 5—Cl | S | Cyclohexyl | |
| 2.50 | 6 | 5—Cl | —SO₂— | Cyclohexyl | |
| 2.51 | 6 | H | —SO₂ | —CH₂—CHBr—CH₃ | |
| 2.52 | 4 | 6—CH₃ | S | —C₂H₄—O—C₂H₅ | |
| 2.53 | 6 | H | O | Cyclohexyl | |
| 2.54 | 6 | H | O | —CH₂—CH=CH₂ | |
| 2.55 | 4 | 6—C₂H₅O | O | —C₂H₅ | |
| 2.56 | 7 | 6—Br | O | —CH₃ | |
| 2.57 | 6 | 5—Cl | O | —CH₂—  | |
| 2.58 | 4 | 6—C₂H₅O— | —N(—nC₃H₇)₂ | | |
| 2.59 | 6 | 5—Cl | —N(CH₃)—CH₂—CH₂—OH | | |
| 2.60 | 6 | H | —N(CH₃)—CH₂—CH₂—N(CH₃)₂ | | |
| 2.61 | 6 | H |  | | |
| 2.62 | 6 | H |  | | |
| 2.63 | 6 | H | —N(C₂H₅)₂ | | |

| Compound No. | SCN— position | R₂ | Y | R₁ | Physical data |
|---|---|---|---|---|---|
| 2.64 | 6 | H | O | —n—C₄H₉ | M.P. 58–59°C |
| 2.65 | 6 | H | O | iso—C₃H₇ | M.P. 80–81°C |
| 2.66 | 6 | H | O | CH₃ | M.P. 98–103°C |
| 2.67 | 6 | H | S | CH₃ | M.P. 94–95°C |
| 2.68 | 6 | H | S | C₂H₅ | M.P. 67–72°C |
| 2.69 | 6 | H | S | —n—C₄H₉ | M.P. 64–67°C |
| 2.70 | 6 | H | —SO₂ | CH₃ | M.P. 159–160°C |
| 2.71 | 6 | H | O | Cyclooctyl | M.P. 55–58°C |
| 2.72 | 6 | H | O | 4-Methylcyclohexyl- | M.P. 95–97°C |
| 2.73 | 6 | H | S | —H | |
| 2.74 | 6 | H | S | —n—octyl | M.P. 62–64°C |
| 2.75 | 6 | H | O | —H | M.P. 227–230°C |
| 2.76 | 6 | H | O | (2-Methoxy)-ethyl | M.P. 119–122°C |
| 2.77 | 6 | H | —N(CH₃)— | —CH₃ | M.P. 137–138°C |
| 2.78 | 6 | H | —N(nC₄H₉)— | —n—C₄H₉ | M.P. 66–68°C |
| 2.79 | 6 | H | —N⟨⟩N—CH₃ | | M.P. 170°C |
| 2.80 | 6 | H | —N⟨⟩N⊕(CH₃)₂ | | M.P. 252–256°C |
| 2.81 | 6 | H | —N⟨(CH₂)₆⟩ | | |

EXAMPLE 6

Production of 5(6)-isothiocyano-2-methyl-benzimidazole (Compound No. 3.2)

A solution of 54.4 g of sodium bicarbonate in 800 ml of water and a solution of 37.5 g of thiophosgene in 67 ml of chloroform are added dropwise at the same time at 0°–5°C, with stirring, to a mixture of 40 g of 5(6)-amino-2-methyl-benzimidazole, 270 ml of chloroform, and 67 ml of water, the addition procedure being such that the mixture remains neutral.

After 7 hours' stirring at 0°–5°C, the suspension is filtered under suction, and subsequently washed with chloroform and a little water. The moist suction-filter residue, dissolved cold in 800 ml of alcohol, is filtered through Hyflosupercel, cooled to 0°C, and afterwards precipitated with 1000 ml of water. The precipitate is filtered off with suction, and dried at 45°C/12 Torr. There is thus obtained 5(6)-isothiocyano-2-methyl-benzimidazole, M.P. 217°–219°C.

Production of 2-n-propylthio-5(6)-isothiocyano-benzimidazole (Compound No. 3.48)

A solution of 19.3 g of thiophosgene in 30 ml of acetone is added dropwise at 0°C, with stirring, to a mixture of 30.8 g of 5(6)-amino-2-n-propylthio-benzimidazole with
300 ml of acetone and
32.5 g of calcium carbonate,
and the whole subsequently stirred at 0°C for 4 hours.

The precipitate is filtered off under suction, stirred with dilute acetic acid, extracted with ethyl acetate, and treated with active charcoal; it is afterwards filtered off from the charcoal, diluted with petroleum ether, and again filtered off. The solution is distilled off to dryness, the residue dissolved in hot acetonitrile and diluted with water. There is obtained, after cooling and filitration under suction, the compound 2-n-propylthio-5(6)-isothiocyano-benzimidazole M.P. 142°–145°C.

It is possible to obtain, in the same manner as described in the examples, or by one of the methods previously indicated, the following isothiocyano-benzimidazoles of formula Ic:

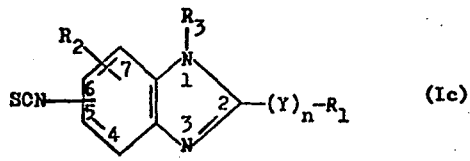

(Ic)

($n = 0$, $R_3 = H$; then the 5- and 6-position as well as the 4- and 7-position are identical, provided also $R_2 = H$) from which corresponding acid addition salts are obtainable:

| Compound No. | SCN— position | R₂ | R₁ | Physical data |
|---|---|---|---|---|
| 3.1. | 6(5) | H | H | M.P. 214–216°C |
| 3.2. | 6(5) | H | CH₃ | M.P. 218–220°C |
| 3.3. | 6(5) | H | iso—C₃H₇ | M.P. 210–212°C |
| 3.3.a | 6(5) | H | iso—C₃H₇ | Hydrochloride M.P. 260°C |
| 3.4. | 6(5) | H | CH₂OCH₃ | M.P. 190–192°C |
| 3.5. | 6(5) | H | CH₂OC₂H₅ | M.P. 141–143°C |
| 3.6. | 6(5) | H | CH=CH—CH₃ | |

| Compound No. | SCN—position | $R_2$ | $R_1$ | Physical data |
|---|---|---|---|---|
| 3.7. | 6(5) | H | —C=CH$_2$ | |
| 3.8. | 6(5) | H | CH$_3$<br>—CH$_2$OH | M.P. 250°C (Hydrochloride) |
| 3.8.a | 6(5) | H | —CH$_2$OH | M.P. 250°C |
| 3.9. | 6(5) | H | —(CH$_2$)$_3$OH | M.P. 157–158°C |
| 3.9.a | 6(5) | H | —(CH$_2$)$_3$OH | Hydrochloride M.P. 212–215°C |
| 3.9.b | 6(5) | H | Glucosyl | M.P. 200°C |
| 3.9.c | 6(5) | H | Glucosyl | (Hydrochloride) M.P. 203–205°C |
| 3.10 | 4(7) | H | CH$_3$ | |
| 3.11 | 6(5) | 5(6)—Cl | iso—C$_3$H$_7$ | |
| 3.12 | 6(5) | 5(6)—CH$_3$ | —n—C$_5$H$_{11}$ | |
| 3.13 | 6(5) | 5(6)CH$_3$CO— | tert.C$_4$H$_9$ | |
| 3.14 | 6(5) | 5(6)CH$_3$O— | H | |
| 3.15 | 6(5) | 5(6)CH$_3$O— | Cyclopropyl | |
| 3.16 | 6(5) | 5(6)Cl | —n—C$_3$H$_7$ | M.P. 174–177°C | as well as compounds of formula Ic with $R_2$=H and n=0:

as well as following compounds of formula Ic with $R_2$=H and n=1:

| Compound No. | SCN—position | $R_3$ | $R_1$ | Physical data |
|---|---|---|---|---|
| 3.12 | 4 | CH$_3$ | H | |
| 3.13 | 4 | CH$_3$ | CH$_3$ | |
| 3.14 | 4 | CH$_3$ | —n—C$_3$H$_7$ | |
| 3.15 | 4 | CH$_3$ | tert.C$_4$H$_9$ | |
| 3.16 | 4 | CH$_3$ | —n—C$_5$H$_{11}$ | |
| 3.17 | 5 | CH$_3$ | —n—C$_5$H$_{11}$ | |
| 3.18 | 5 | CH$_3$ | CH$_3$ | |
| 3.19 | 6 | CH$_3$ | iso—C$_3$H$_7$ | |
| 3.20 | 6 | CH$_3$ | H | |
| 3.21 | 6 | CH$_3$ | CH$_3$ | |
| 3.22 | 6 | CH$_3$ | —n—C$_4$H$_9$ | |
| 3.23 | 7 | CH$_3$ | H | |
| 3.24 | 7 | CH$_3$ | C$_2$H$_5$ | |
| 3.25 | 6 | C$_2$H$_5$ | CH$_3$ | |
| 3.26 | 6 | —n—C$_4$H$_9$ | CH$_3$ | |
| 3.27 | 6 | Benzyl | CH$_3$ | |
| 3.28 | 6 | Ribo-furanosyl | n—C$_3$H$_7$ | |
| 3.29 | 6 | Acetyl | CH$_3$ | |
| 3.30 | 6 | Glycosyl | CH$_3$ | |
| 3.31 | 6 | Propionyl | CH$_3$ | |
| 3.32 | 6 | Benzoyl | CH$_3$ | |
| 3.33 | 6 | CCl$_3$—CO | CH$_3$ | |
| 3.34 | 6 | C$_2$H$_5$O—CO— | CH$_3$ | |
| 3.35 | 6 | iso—C$_3$H$_7$ | n—Hexyl | |
| 3.36 | 6 | CH$_3$ | Glucosyl | |
| 3.37 | 6 | —C$_2$H$_5$ | Heptaglucosyl | |

| Compound No. | SCN—position | $R_3$ | Y | $R_1$ | Physical data |
|---|---|---|---|---|---|
| 3.38 | 6(5) | H | O | H | |
| 3.39 | 6(5) | H | S | H | |
| 3.40 | 6(5) | H | —NH— | H | |
| 3.41 | 6 | —CH$_3$ | O | CH$_3$ | M.P. 105–109°C |
| 3.42 | 5 | —CH$_3$ | S | C$_2$H$_5$ | |
| 3.43 | 6(5) | H | S | CH$_3$ | |
| 3.44 | 6(5) | H | O | C$_2$H$_5$ | |
| 3.45 | 6(5) | H | O | Octyl | |
| 3.46 | 6(5) | H | O | Cyclopropylmethyl | |
| 3.47 | 6(5) | H | O | —C$_2$H$_4$—O—C$_2$H$_5$ | |
| 3.48 | 6(5) | H | S | —n—C$_3$H$_7$ | M.P. 142–145°C |
| 3.49 | 6(5) | H | S | Cyclohexyl | |
| 3.50 | 6(5) | H | —N(C$_2$H$_5$)— | C$_2$H$_5$ | |
| 3.51 | 6(5) | H | —N(sec.Butyl)— | sec. Butyl | |
| 3.52 | 6 | Benzyl | O | —n—C$_3$H$_7$ | |
| 3.53 | 6 | Allyl | S | —n—C$_3$H$_7$ | |
| 3.54 | 6 | H | —NH— | —CCl$_3$ | |
| 3.55 | 5 | —CH$_3$ | S | —C$_2$H$_5$ | |
| 3.56 | 6(5) | H | —NCH$_3$— | CH$_3$ | M.P. 258–261°C |
| 3.57 | 6 | C$_2$H$_5$ | S | sec.C$_4$H$_9$ | |
| 3.58 | 6 | Benzyl | S | iso—C$_3$H$_7$ | |
| 3.59 | 6 | Acetyl | S | —n—Butyl | |
| 3.60 | 6 | Acetyl | S | Cyclopentyl | |
| 3.61 | 6 | Acetyl | O | C$_2$H$_5$ | |
| 3.62 | 6 | H$_5$C$_2$O—CO— | O | C$_2$H$_5$ | |
| 3.63 | 6 | Acetyl | O | Cyclopropyl | |

| Compound No. | SCN— position | R₃ | Y | R₁ | Physical data |
|---|---|---|---|---|---|
| 3.64 | 6 | H | | -N(pyrrolidinyl) | |
| 3.65 | 6 | H | | -N(piperidinyl) | |
| 3.66 | 6 | H | | -N(morpholinyl) | |
| 3.67 | 6 | | Acetyl | -N(piperidinyl) | |
| 3.68 | 6 | | CH₃ | -N(piperidinyl) | |
| 3.69 | 6 | | Benzyl | -N(piperidinyl) | |
| 3.70 | 5 | | Acetyl | -N(piperidinyl) | |
| 3.71 | 6 | | —n—C₄H₉ | -N(morpholinyl) | | as well as the compounds 3.72 2-(4'-methylpiperidino)-1-ethyl-6-trifluoromethyl-5-isothiocyano-benzimidazole, 3.73 2-trifluoromethyl-1-benzyl-7-chloro-5-isothiocyano-benzimidazole, 3.74 2-methyl-1-ethyl-6-trifluoromethyl-5-isothiocyano-benzimidazole.

3.75 1,2,6-trimethyl-5-isothiocyano-benzimidazole, 3.76 1,2,5-trimethyl-6-isothiocyano-benzimidazole, 3.77 2-(1-cyclohexenyl)-1-diethylaminoethyl-6-isothiocyano-benzimidazole, 3.78 1-methoxycarbonyl-2-n-propyl-6-chloro-5-isothiocyano-benzimidazole, M.P. 88°–92°C, 3.79 1-methoxycarbonyl-2-cyclopentylthio-5(6)-isothiocyano-benzimidazole, M.P. 118°–122°C, 3.80 2-isopropylthio-5(6)-isothiocyano-benzimidazole M.P. 159°–162°C, 3.81 1-ethoxycarbonyl-2-n-butylthio-5(6)-isothiocyano-benzimidazole, M.P. 59°–62°C 3.82 1-n-butoxycarbonyl-2-methylthio-5(6)-isothiocyano-benzimidazole, M.P. 77°–80°C, 3.83 1-propionyl-2-isopropylthio-5(6)-isothiocyano-benzimidazole, M.P. 73°–76°C.

Tests on mice infested by Hymenolepsis nana

The active substances in the form of a suspension were administered by stomach probe to white mice infested with Hymenolepsis nana. Five animals per test were used. The active substances were administered to each animal once daily during three successive days. On the eighth day after commencement of the treatment, the animals were killed and dissected.

After dissection of the test animals, an evaluation was made on the basis of a count of the tapeworms present in the intestines. As a control, an examination was also carried out on untreated mice which had been simultaneously and identically infested.

The agents were tolerated asymtomatically by the mice.

| Active substance | Infestation of the 5 test animals on dissection | Infestation of the control animals on dissection |
|---|---|---|
| 2-methyl-6-isothiocyano-benzoxazole (dose: 100 mg AS/kg of body weight | 0 - 0 - 0 - 0 - 0 | 1 - 2 - 4 - 5 - 7 |
| 2-ethyl-5-isothiocyano-benzoxazole (250 mg AS/kg) | 0 - 0 - 0 - 0 - 0 | 26 - 7 - 13 - 19 - 36 |
| 2-Methyl-6-isothiocyano-benzothiazole (750mg AS/kg) | 0 - 0 - 0 - 0 - 0 | 11 - 12 - 12 - 16 - 16 |
| 2-ethyl-6-isothiocyano-benzothiazole (750mg AS/kg) | 0 - 0 - 0 - 0 - 0 | 11 - 12 - 12 - 16 - 16 |
| 2-Isopropyl-6-isothiocyano-benzothiazole (750mg AS/kg) | 0 - 0 - 0 - 0 - 0 | 8 - 99 - 10 - 11 |
| 4-Isothiocyano-benzothiazole (750mg AS/kg) | 0 - 0 - 0 - 0 - 0 | 8 - 9 - 9 - 10 - 11 |
| 5-Isothiocyano-2-n-octyl-benzoxazole (750 mg/kg) | 0 - 0 - 0 - 0 - 0 | 11 - 16 - 20 - 29 - 47 |
| 6-Isothiocyano-2-mercapto-benz- | | |

-continued

| Active substance | Infestation of the 5 test animals on dissection | Infestation of the control animals on dissection |
|---|---|---|
| oxazole (750 mg/kg) | 0 - 0 - 0 - 0 - 0 | 0 - 1 - 2 - 2 - 4 |
| 5-Isothiocyano-2-methylthio-benzoxazole (750 mg/kg | 0 - 0 - 0 - 0 - 0 | 6 - 7 - 9 - 10 - 12 |
| 2-n-Butoxy-6-isothiocyano-benzothiazole (300 mg/kg) | 0 - 0 - 0 - 0 - 0 | 0 - 1 - 2 - 4 - 5 |
| 2-n-Butylthio-6-isothiocyano-benzothiazole (750 mg/kg) | 0 - 0 - 0 - 0 - 0 | 2 - 3 - 10 - 11 - 13 |
| 6-Isothiocyano-2-methylsulfonyl benzothiazole (750 mg/kg) | 0 - 0 - 0 - 0 - 0 | 2 - 3 - 10 - 11 - 13 |
| 6(5)-Isothiocyano-2-n-propyl-thiobenzimidazole (750 mg/kg) | 0 - 0 - 0 - 0 - 1 | 6 - 14 - 15 - 18 - 25 |
| 2-ethoxy-6-isothiocyano-benzoxazole (500 mg/kg) | 0 - 0 - 0 - 0 - 0 | 0 - 3 - 11 - 12 - 14 |

Tests on mice infested by mouse threadworms (oxyuris)

The active substance was administered in the form of a suspension by means of a stomach probe to white mice infested with mouse threadworms. Five animals were used for each test. The active substances were administered to each animal once daily during three successive days. The animals were then killed on the eighth day after commencement of the treatment and dissected.

After dissection of the test animals, an evaluation was made on the basis of the count of mouse threadworms present in the intestines. Untreated mice which had been simultaneously infested served as a control The agents were tolerated asymtomatically by the mice.

| Active substance | Infestation of the test animals on dissection | Infestation of control animals on dissection |
|---|---|---|
| 2-ethyl-5-isothiocyano-benzoxazole dose: 250 mg/kg of body weight | 0 - 0 - 0 - 0 - 0 | 5 - 4 - 4 - 9 - 9 |
| 2-cyclohexyl-5-isothiocyano-benzoxazole (750 mg/kg) | 0 - 0 - 0 - 0 - 0 | 0 - 4 - 13 - 29 - 42 |
| 2-(n-Amyl)-6-isothiocyano-benzothiazole (750 mg/kg) | 0 - 0 - 0 - 0 - 0 | 2 - 4 - 4 - 5 - 13 |
| 2-Isopropyl-6-isothiocyano-benzothiazole (750 mg/kg) | 0 - 0 - 0 - 0 - 0 | 2 - 14 - 20 |
| 4-Isothiocyano-benzothiazole (750 mg/kg) | 0 - 0 - 0 - 0 - 0 | 2 - 14 - 20 |
| 5-Isothiocyano-2-n-octyl-benzoxazole (750 mg/kg) | 0 - 0 - 0 - 0 - 1 | 1 - 3 - 25 - 30 - 53 |
| 2-ethoxy-6-isothiocyano-benzoxazole (750 mg/kg) | 0 - 0 - 0 - 0 - 0 | 4 - 9 - 15 - 21 - 32 |
| 2-Isopropylthio 5-isothiocyano-benzoxazole (750 mg/kg) | 0 - 0 - 0 - 0 - 0 | 8 - 8 - 14 - 15 - 20 |
| 5-Isothiocyano-2-methylthio benzoxazole (750 mg/kg) | 0 - 0 - 0 - 0 - 0 | 20 - 10 - 12 - 18 - 24 |
| 2-n-Butoxy-6-isothiocyano-benzothiazole (300 mg/kg) | 0 - 0 - 0 - 0 - 0 | 1 - 2 - 3 - 3 - 4 |
| 6-Isothiocyano-2-methylthio benzothiazole (500 mg/kg) | 0 - 0 - 0 - 0 - 0 | 1 - 2 - 3 - 3 - 4 |
| 2-ethylthio- | | |

-continued

| Active substance | Infestation of the test animals on dissection | Infestation of control animals on dissection |
|---|---|---|
| 6-isothiocyano benzothiazole (500 mg/kg) | 0 - 0 - 0 - 0 - 0 | 2 - 2 - 16 - 35 - 40 |
| 1-Methoxycarbonyl-2-n-propyl-5-chloro-6-isothiocyano-benzimidazole (750 mg/kg) | 0 - 0 - 0 - 0 - 0 | 7 - 8 - 18 - 26 - 40 |

The agents were tolerated asymtomatically by the mice.

| Active substance | Infestation of the 5 test animals on dissection | Infestation of control animals on dissection |
|---|---|---|
| 2-ethyl-5-isothiocyano-benzoxazole (250 mg of active substance per kg of body weight) | 0 - 0 - 0 - 0 - 1 | 22 - 10 - 10 - 16 - 16 |
| 2-n-amyl-6-isothiocyano-benzoxazole (750 mg/kg) | 0 - 0 - 0 - 0 - 0 | 7 - 9 - 11 - 14 - 20 |
| 6-Isothiocyano-2-methyl-benzothiazole (750 mg/kg) | 0 - 0 - 0 - 0 - 0 | 12 - 12 - 18 - 23 - 25 |
| 2-Isopropyl-6-iosthiocyano-benzothiazole (750 mg/kg) | 0 - 0 - 0 - 0 - 0 | 4 - 9 - 11 |
| 5-Isothiocyano-2-n-octyl-benzoxazole (750 mg/kg) | 0 - 0 - 0 - 0 - 3 | 4 - 9 - 11 - 14 - 17 |
| 5-isothiocyano-2-methyl-benzoxazole (250 mg/kg) | 0 - 0 - 0 - 0 - 2 | 7 - 8 - 8 - 9 - 10 |
| (2-ethoxy-6-isothiocyano-benzoxazole (750 mg/kg) | 0 - 0 - 0 - 0 - 0 | 4 - 10 - 13 - 15 - 15 |
| 2-Isopropylthio-5-isothiocyano-benzoxazole (750 mg/kg) | 0 - 0 - 0 - 0 - 0 | 13 - 14 - 18 - 20 - 24 |
| 5-Isothiocyano-2-methylthio-benzoxazole (750 mg/kg) | 0 - 0 - 0 - 0 - 0 | 7 - 7 - 9 - 10 - 11 |
| 6-Isothiocyano-2-methoxy-benzothiazole (750 mg/kg) | 0 - 0 - 0 - 0 - 0 | 19 - 21 - 22 - 27 |
| 6-Isothiocyano-2-methylthio-benzothiazole (500 mg/kg) | 0 - 0 - 0 - 0 - 0 | 18 - 18 - 21 - 22 - 27 |
| 2-ethylthio-6-isothiocyano-benzothiazole (500 mg/kg) | 0 - 0 - 0 - 0 - 0 | 7 - 9 - 11 - 12 - 13 |

Tests on mice infested by Nematospiroides dubius

The acitve substances in the form of a suspension were administered by a stomach probe to white mice which had been infested with Nematospiroides dubius. Five animals per test were used. The active substances were administered to each animal once daily on three successive days. On the eighth day after commencement of the treatment, the animals were killed and dissected.

After dissection of the test animals, an evaluation was made on the basis of the count of worms present in the intestines. Untreated mice which had been simultaneously and identically infested served as a control.

Tests on rats infested by Fasciola hepatica

White laboratory-rats were infested with common liver flukes (*Fasciola hepatica*). After expiration of the prepatent period, the infestation of the rats by common liver flukes was determined by means of three independent excrement analyses.

In each test, two infested rats were treated in each case with the active substance, administered in the form of a suspension by stomach probe, once daily on three successive days. An excrement analysis to determine the content of common liver fluke eggs was made once weekly in the third, fourth and fifth week after administration of the active substance. At the end of the fifth week after commencement of the test, the test animals were killed and examined to determine whether liver flukes were still present.

for each test. 4–5 Weeks after infestation, the active substances were administered to the chickens in the form of one daily dose on three successive days. Infested but untreated birds served as a control.

| Active substance | Daily dosage in mg/kg of body weight | Excrement examination for eggs (3×) | |
|---|---|---|---|
| | | before medication | after medication |
| 2-Methyl-6-isothiocyano-benzoxazole | 100 | positive | negative |
| 2-ethyl-5-isothiocyano-benzoxazole | 50 | positive | negative |
| 2-(n-Amyl)-6-isothiocyano-benzoxazole | 50 | positive | negative |
| 2-Cyclohexyl-5-isothiocyano-benzoxazole | 100 | positive | negative |
| 2-ethyl-6-iso-thiocyano-benzo-thiazole | 100 | positive | negative |
| 2-Isopropyl-6-isothiocyano-benzo-thiazole | 100 | positive | negative |
| 5-Isothiocyano-2-n-octyl-benzoxa-zole | 150 | positive | negative |
| 6-Isothiocyano-2-mercapto-benz-oxazole | 100 | positive | negative |
| 2-Isopropylthio-5-isothiocyano-benzoxazole | 100 | positive | negative |
| 5-Isothiocyano-2-methylthio-benzoxa-zole | 100 | positive | negative |
| 2-Isopropoxy-6-iso-thiocyano-benzothia-zole | 50 | positive | negative |
| 6-Isothiocyano-2-methylthio-benzothia-zole | 200 | positive | negative |
| 2-ethylthio-6-isothiocyano-benzo-thiazole | 200 | positive | negative |

The control test for liver flukes after dissection was negative in all cases.

Determination of the anthelmintic action on fowl infested with *Ascaridia galli*

1–3 Day-old chickens were infested with eggs of *Ascaridia galli* (ascarides). A group of 5 chickens was used The number of Ascardia galli excreted by each test group in the course of 5 days after the first administration was determined daily, and the number of worms still present in the intestines following dissection on the 5 th day of the test likewise counted. The number of chickens free from worms was also determined.

| Active substance | Daily dose in mg/kg of body weight | Number of Ascaridia galli from 5 chickens | |
|---|---|---|---|
| | | excreted | found after dissection |
| 2-methyl-6-iso-thiocyanobenzo-thiazole | 750 | 49 | 0 - 0 - 0 - 0 - 0 |
| 2-ethyl-6-iso-thiocyanobenzo-thiazole | 750 | 41 | 0 - 0 - 0 - 1 - 0 |
| 2-ethyl-6-iso-thiocyanobenzo-thiazole-hydro-chloride | 750 | 79 | 0 - 0 - 0 - 0 - 0 |
| 2-(n-Amyl)-6-iso-thiocyanobenzothia-zole | 750 | 66 | 0 - 0 - 0 - 0 - 0 |
| 2-Isopropyl-6-isothiocyanobenze-thiazole | 750 | 63 | 0 - 0 - 0 - 0 - 0 |
| 2-methyl-6-iso-thiocyano-benz-oxazole | 500 | 26 | 0 - 0 - 0 - 0 - 10 |
| 2-(n-Amyl)-6-isothiocyano-benzoxazole | 750 | 119 | 0 - 0 - 0 - 0 - 0 |
| 2-n-Octyl-6-isothiocyano-benzoxazole | 750 | 116 | 0 - 0 - 0 - 0 - 0 |
| 2-ethoxy-6-isothiocyano- | 750 | 103 | 0 - 0 - 0 - 0 - 7 |

-continued

| Active substance | Daily dose in mg/kg of body weight | Number of excreted | Ascaridia galli from 5 chickens found after dissection |
|---|---|---|---|
| benzoxazole 2-Cyclohexyl-thio-6-isothio-cyano-benzoxazole | 750 | 84 | 0 - 0 - 0 - 1 - 4 |
| 6-Isothiocyano-2-methoxy-benzthiazole | 750 | 143 | 0 - 0 - 0 - 1 - 3 |
| 6-Isothiocyano-2-methylthio-benzothiazole | 500 | 131 | 0 - 0 - 0 - 0 - 0 |
| 6-Isothiocyano-2-ethyl-thiobenzothiazole | 500 | 181 | 0 - 0 - 0 - 0 - 0 |
| 6-Isothiocyano-2-n-butylthio-benzothiazole | 750 | 145 | 0 - 0 - 0 - 0 - 0 |
| 6(5)-chloro 5(6)-isothio-cyano-2-n-propyl-benzimidazole | 750 | 65 | 0 - 0 - 0 - 0 - 5 |

Action against pathogenic bacteria and fungi.

Determination of the minimum inhibition concentration (MIC)

Samples of a dilution series (commencing at 100 ppm) of active substance dissolved in methylcellosolve are intimately mixed at ca. 50°C with liquid agar. The warm mixture is poured into glass dishes of 10 cm diameter to form a 0.5 cm deep layer, and then allowed to cool. The cultures of bacteria and of fungi are then applied in the form of points by means of an automatic dosing device, the concentration being from $10^6$ to $10^7$ germs per ml. The dishes are kept in an incubator at 37°C.

The following gram-positive strains of bacteria were examined:
Staphylococcus aureus K 465
Staphylococcus aureus K 444
Staphylococcus aureus K 443
Staphylococcus aureus M 6
Streptococcus agalactiae M 100
Streptococcus agalactiae M 101
Erysipelothrix rhusiopathiae K 593
Listeriae monocytogenes Type IV-b The following gram-negative strains of bacteria were examined:
Escherichia coli G 70/1172
Escherichia coli 139:82.B
Escherichia coli 78:80.B
Escherichia coli M 155
Escherichia coli 7:1.7,8
Salmonella gallinarum VBIB
Salmonella cholerae suis VBIB
Salmonella pullorum typhimurium VBIB
Salmonella multocida K 753
Brucella suis VBIB
Proteus rettgeri 107-153-1
Klebsiella pneumoniae 107-153-3

The following strains of fungi were examined:
Aspergillus niger K 617
Candida pseudotropicalis CDC 48
Candida krusei CDC 46
Candida Krusei M 500
Pseudomonas sp.
Trichophyton gallinae K 454
Trichophyton verrucosum K 424
Trichophyton quinckeanum K 883
Hefe M 500
Hefe M 501

An evaluation was made after 24 hours. Values of minimum inhibition concentration were obtained for compounds of formula I which were clearly below the starting concentration of 100 ppm.

The following examples describe the production of preparations of anthelmintically effective agents and feed additives. The term 'parts' denotes parts by weight.

Dispersible powder

The following constituents are used in the preparation of 50% dispersible powders:

a)  50 parts of an active substance according to the invention,
    1 part of a polyethyleneoxypropylene glycol having a molecular weight of ca. 2000 (Pluronic L 61),
    5 parts of the ammonium salt of a sulphonated naphthalene sulphonic acid/phenol formaldehyde condensate (Irgatan AG1),
    44 parts of kaolin;
b)  50 parts of an active substance according to the invention,
    1 part of a polyethyleneoxypropylene glycol having a molecular weight of ca. 8000 (Pluronic F 68),
    0.5 part of sodium lignin sulphate,
    48.5 parts of sodium silicate.

The given active substances are mixed with the carriers and distributing agents and then finely ground. The obtained powder can be mixed with liquid or pasty feeding stuffs and thus administered to domestic and useful animals.

Paste

The following substances are used in the preparation of a 40% paste:

| | |
|---|---|
| 40 | parts of active substance according to the invention, |
| 2.5 | parts of sodium lignin sulphonate, |
| 0.3 | part of sodium benzoate, |
| 10 | parts of glycerin, |
| 47.2 | parts of distilled water. |

The active substance and the distributing agents are intimately mixed. The thus obtained paste is mixed with liquid and pasty feeding stuffs for administration to domestic and useful animals.

Feed additive press cakes

The following substances are used in the preparation of 35% feed additive press cakes:

| | |
|---|---|
| 35 | parts of active substance according to the invention, |
| 15 | parts of molasses, |
| 5 | parts of licorice powder, |
| 25 | parts of dried green meal, |
| 20 | parts of ground bran. |

The active substance and the distributing agents are mixed and formed into press cakes in an animal-feed press. The obtained feed additive concentrate is mixed with the feeding stuffs and thus administered to domestic and useful animals.

Emulsifiable concentrate

An emulsifiable concentrate is obtained by the mixing together of the following constituents:

| | |
|---|---|
| 2 | parts of active substance according to the invention, |
| 2 | parts of a polyethyleneoxypropylene glycol having a molecular weight of ca. 3000 (Pluronic L 64), and |
| 96 | parts of acetone. |

The obtained concentrate can be diluted with water to give emulsions of any desired concentration, and thus administered, e.g. as drink to domestic and productive animals.

Oily formulation

| | |
|---|---|
| 40 | parts of active substance according to the invention are ground as finely as possible in a suitable mill, and subsequently homogeneously mixed, e.g. on a roll mill, with |
| 60 | parts of arachis oil (peanut oil) |

These oil-pastes can be administered orally to the animals.

We claim:
1. An anthelmintic composition comprising (a) as active ingredient, an anthelmintically effective amount of a compound of the formula

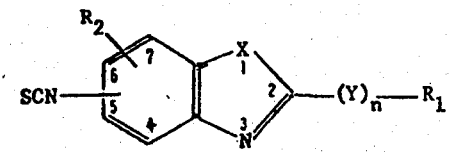

wherein the SCN-group is in the 4-, 5-, 6- or 7-position,
R₁ represents hydrogen, a straight-chain or branched alkyl or alkenyl radical having at most 17 carbon atoms, an alkyl or alkenyl radical having a total of at most 6 carbon atoms and substituted by halogen, —CN, —OH, C₁–C₅ alkoxy, C₁–C₅ alkylthio or di-(C₁–C₅)alkylamino, an optionally C₁–C₅ alkyl-substituted mono-, bi- or tricyclic cycloalkyl or cycloalkenyl radical having 3 to 10 carbon atoms in the ring structure, which can also be bound by way of a CH₂-group to the substituent Y or to the 2-position of the heterocycle,
R₂ represents hydrogen, halogen or an alkyl or alkoxy radical having at most 4 carbon atoms,
X represents oxygen, sulphur or

R₃ represents hydrogen, an alkyl or alkenyl radical having at most 5 carbon atoms, a phenyl or benzyl radical, a dimethylamino- or diethylamino-alkyl radical having 2 – 5 carbon atoms in the alkyl chain, an alkoxycarbonyl radical having 2 – 5 carbon atoms, acetyl, propionyl, trichloroacetyl, benzoyl, or a C₄–C₇ saccharide group,
Y represents oxygen, sulphur, —SO—, —SO₂—, or —NR₄—,
n is the number 0 or 1,
R₄ represents hydrogen, an alkyl or alkenyl radical having at most 5 carbon atoms, or together with the N-atom and the substituent R₁ a saturated or unsaturated heterocycle having 4 to 6 carbon atoms which may also contain a further hetero atom O or S selected from the group consisting of pyrrolidine, piperidine, 2-methylpiperidine, 4-methylpiperidine, piperazine, N'-methyl, N',N'-dimethyl and N'-ethyl-piperazine, morpholine, isomorpholine, thiomorpholine and hexamethyleneimine, or the group

and
R₅ stands for hydrogen, methyl or ethyl,
or their acid addition salts non-toxic for warm-blooded animals together with (b) a carrier.

2. The composition of claim 1, wherein said compound corresponds to the formula

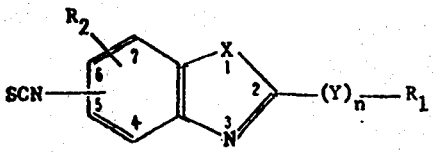

wherein the SCN-group is in the 5- or 6-position and
R₁ represents hydrogen, a straight-chain or branched alkyl or alkenyl radical having at most 17 carbon atoms, an alkyl or alkenyl radical having a total of at most 6 carbon atoms and substituted by halogen, —CN, —OH, C₁–C₅ alkoxy, C₁–C₅ alkylthio or di-(C₁–C₅)alkylamino, an optionally C₁–C₅ alkyl-substituted mono-, bi- or tricyclic cycloalkyl or cycloalkenyl radical having 3 to 10 carbon atoms in the ring structure, which can also be bound by way of a CH₂-group to the substituent Y or to the 2-position of the heterocycle, $R_2$ represents hydrogen, halogen or an alkyl or alkoxy radical having at most 4 carbon atoms, X represents oxygen, sulphur or

$R_3$ represents hydrogen, an alkyl or alkenyl radical having at most 5 carbon atoms, a phenyl or benzyl radical, a dimethylamino- or diethylamino-alkyl radical having 2 – 5 carbon atoms in the alkyl chain, an alkoxycarbonyl radical having 2 – 5 carbon atoms, acetyl, propionyl, trichloroacetyl, benzoyl, or a $C_4$–$C_7$ saccharide group, Y represents oxygen, sulphur, —SO—, —$SO_2$—, or —$NR_4$—, $n$ is the number 0 or 1, $R_4$ represents hydrogen, an alkyl or alkenyl radical having at most 5 carbon atoms, or together with the N-atom and the substituent $R_1$ a saturated or unsaturated heterocycle having 4 to 6 carbon atoms which may also contain a further hetero atom O or S selected from the group consisting of pyrrolidine, piperidine, 2-methylpiperidine, 4-methylpiperidine, piperazine, N'-methyl,N', N'-dimethyl and N'-ethyl-piperazine, morpholine, isomorpholine, thiomorpholine and hexamethyleneimine, or the group

and $R_5$ stands for hydrogen, methyl or ethyl.

3. The composition of claim 2, wherein said compound corresponds to the formula

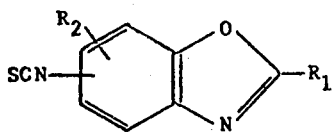

wherein $R_1$ represents hydrogen, a straight-chain or branched alkyl or alkenyl radical having at most 17 carbon atoms, an alkyl or alkenyl radical having a total of at most 6 carbon atoms and substituted by halogen, —CN, —OH, $C_1$–$C_5$ alkoxy, $C_1$–$C_5$ alkylthio or di-($C_1$–$C_5$)alkylamino, an optionally $C_1$–$C_5$ alkyl-substituted mono-, bi- or tricyclic cycloalkyl or cycloalkenyl radical having 3 to 10 carbon atoms in the ring structure, which can also be bound by way of a $CH_2$-group to the 2-position of the heterocycle, and $R_2$ represents hydrogen, halogen or an alkyl or alkoxy radical having at most 4 carbon atoms.

4. The composition of claim 2, wherein said compound corresponds to the formula

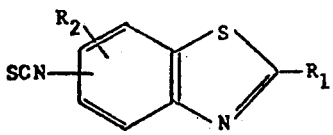

wherein $R_1$ represents hydrogen, a straight-chain or branched alkyl or alkenyl radical having at most 17 carbon atoms, an alkyl or alkenyl radical having a total of at most 6 carbon atoms and substituted by halogen, —CN, —OH, $C_1$–$C_5$ alkoxy, $C_1$–$C_5$ alkylthio or di-($C_1$–$C_5$)alkylamino, an optionally $C_1$–$C_5$ alkyl-substituted mono-, bi- or tricyclic cycloalkyl or cycloalkenyl radical having 3 to 10 carbon atoms in the ring structure, which can also be bound by way of a $CH_2$-group to the 2-position of the heterocycle, and $R_2$ represents hydrogen, halogen or an alkyl or alkoxy radical having at most 4 carbon atoms.

5. A method for the control of parasitic helminthes which comprises administering orally or abomasally to a warm-blooded animal infested therewith an anthelmintically effective amount of a compound of the formula

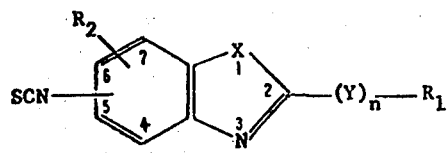

wherein the SCN-group is in the 4-, 5-, 6- or 7- position, $R_1$ represents hydrogen, a straight-chain or branched alkyl or alkenyl radical having at most 17 carbon atoms, an alkyl or alkenyl radical having a total of at most 6 carbon atoms and substituted by halogen, —CN, —OH, $C_1$–$C_5$ alkoxy, $C_1$–$C_5$ alkylthio or di-($C_1$–$C_5$)alkylamino, an optionally $C_1$–$C_5$ alkyl-substituted mono-, bi- or tricyclic cycloalkyl or cycloalkenyl radical having 3 to 10 carbon atoms in the ring structure, which can also be bound by way of a $CH_2$-group to the substituent Y or to the 2-position of the heterocycle.

$R_2$ represents hydrogen, halogen or an alkyl or alkoxy radical having at most 4 carbon atoms, X represents oxygen, sulphur or

$R_3$ represents hydrogen, an alkyl or alkenyl radical having at most 5 carbon atoms, a phenyl or benzyl radical, a dimethylamino- or diethylamino-alkyl radical having 2 – 5 carbon atoms in the alkyl chain, an alkoxycarbonyl radical having 2 – 5 carbon atoms, acetyl, propionyl, trichloroacetyl, benzoyl, or a $C_4$–$C_7$ saccharide group, Y represents oxygen, sulphur, —SO—, —$SO_2$—, or —$NR_4$—, $n$ is the number 0 or 1, $R_4$ represents hydrogen, an alkyl or alkenyl radical having at most 5 carbon atoms, or together with the N-atom and the substituent $R_1$ a saturated or unsaturated heterocycle having 4 to 6 carbon atoms which may also contain a further hetero atom O or S selected from the group consisting of pyrrolidine, piperidine, 2-methylpiperidine, 4-methylpiperidine, piperazine, N'-methyl, N',N'-dimethyl and N'-ethyl-piperazine, morpholine, isomorpholine, thiomorpholine and hexamethyleneimine, or the group

and $R_5$ stands for hydrogen, methyl or ethyl,
or their acid addition salts non-toxic for warm-blooded animals.

6. The method of claim 5, wherein said compound corresponds to the formula

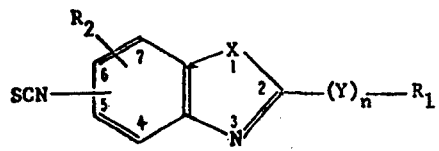

wherein the SCN-group is in the 5- or 6-position and
$R_1$ represents hydrogen, a straight-chain or branched alkyl or alkenyl radical having at most 17 carbon atoms, an alkyl or alkenyl radical having a total of at most 6 carbon atoms and substituted by halogen, —CN, —OH, $C_1$–$C_5$ alkoxy, $C_1$–$C_5$ alkylthio or di-($C_1$–$C_5$)alkylamino, an optionally $C_1$–$C_5$ alkyl-substituted mono-, bi- or tricyclic cycloalkyl or cycloalkenyl radical having 3 to 10 carbon atoms in the ring structure, which can also be bound by way of a $CH_2$-group to the substituent Y or to the 2-position of the heterocycle,
$R_2$ represents hydrogen, halogen or an alkyl or alkoxy radical having at most 4 carbon atoms,
X represents oxygen, sulphur or

$R_3$ represents hydrogen, an alkyl or alkenyl radical having at most 5 carbon atoms, a phenyl or benzyl radical, a dimethylamino- or diethylamino-alkyl radical having 2 – 5 carbon atoms in the alkyl chain, an alkoxycarbonyl radical having 2 – 5 carbon atoms, acetyl, propionyl, trichloroacetyl, benzoyl, or a $C_4$–$C_7$ saccharide group,
Y represents oxygen, sulphur, —SO, —$SO_2$—, or —$NR_4$—,
n is the number 0 or 1,
$R_4$ represents hydrogen, an alkyl or alkenyl radical having at most 5 carbon atoms, or together with the N-atom and the substituent $R_1$ a saturated or unsaturated heterocycle having 4 to 6 carbon atoms which may also contain a further hetero atom 0 or S selected from the group consisting of pyrrolidine, piperidine, 2-methylpiperidine, 4-methylpiperidine, piperazine, N'-methyl, N', N'-dimethyl and N'-ethyl-piperazine, morpholine, isomorpholine, thiomorpholine and hexamethyleneimine, or the group

and $R_5$ stands for hydrogen, methyl or ethyl.

7. The method of claim 6, wherein said compound corresponds to the formula

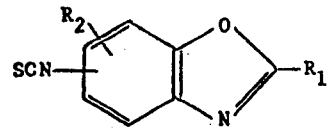

wherein
$R_1$ represents hydrogen, a straight-chain or branched alkyl or alkenyl radical having at most 17 carbon atoms, an alkyl or alkenyl radical having a total of at most 6 carbon atoms and substituted by halogen, —CN, —OH, $C_1$–$C_5$ alkoxy, $C_1$–$C_5$ alkylthio or di-($C_1$–$C_5$)alkylamino, an optionally $C_1$–$C_5$ alkyl-substituted mono-, bi- or tricyclic cycloalkyl or cycloalkenyl radical having 3 to 10 carbon atoms in the ring structure, which can also be bound by way of a $CH_2$-group to the 2-position of the heterocycle, and
$R_2$ represents hydrogen, halogen or an alkyl or alkoxy radical having at most 4 carbon atoms.

8. The method of claim 6, wherein said compound corresponds to the formula

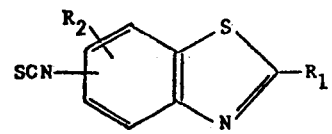

wherein
$R_1$ represents hydrogen, a straight-chain or branched alkyl or alkenyl radical having at most 17 carbon atoms, an alkyl or alkenyl radical having a total of at most 6 carbon atoms and substituted by halogen, —CN, OH, $C_1$–$C_5$ alkoxy, $C_1$–$C_5$ alkylthio or di-($C_1$–$C_5$)alkylamino, an optionally $C_1$–$C_5$ alkyl-substituted mono-, bi- or tricyclic cycloalkyl or cycloalkenyl radical having 3 to 10 carbon atoms in the ring structure, which can also be bound by way of a $CH_2$-group to the 2-position of the heterocycle, and
$R_2$ represents hydrogen, halogen or an alkyl or alkoxy radical having at most 4 carbon atoms.

* * * * *